(12) United States Patent
McDonell

(10) Patent No.: US 11,879,114 B2
(45) Date of Patent: Jan. 23, 2024

(54) SUSTAINABLE GREEN SOLID POTASSIUM FATTY ACID SOAPS AND SELF THICKENING LIQUID SOAPS MADE THEREOF

(71) Applicant: James Arthur McDonell, Pine City, MN (US)

(72) Inventor: James Arthur McDonell, Pine City, MN (US)

( * ) Notice: Subject to any disclaimer, the term of this patent is extended or adjusted under 35 U.S.C. 154(b) by 2 days.

(21) Appl. No.: 18/139,706

(22) Filed: Apr. 26, 2023

(65) Prior Publication Data

US 2023/0357675 A1 Nov. 9, 2023

Related U.S. Application Data

(60) Provisional application No. 63/338,606, filed on May 5, 2022.

(51) Int. Cl.
| | |
|---|---|
| *A61K 8/00* | (2006.01) |
| *C11D 9/02* | (2006.01) |
| *A61K 8/19* | (2006.01) |
| *C11D 11/00* | (2006.01) |
| *A61Q 19/10* | (2006.01) |
| *C11D 9/10* | (2006.01) |
| *A61K 8/36* | (2006.01) |

(52) U.S. Cl.
CPC ............ *C11D 9/02* (2013.01); *A61K 8/19* (2013.01); *A61K 8/361* (2013.01); *A61Q 19/10* (2013.01); *C11D 9/10* (2013.01); *C11D 11/0082* (2013.01)

(58) Field of Classification Search
CPC .................................... C11D 9/02; A61K 8/19
See application file for complete search history.

(56) References Cited

U.S. PATENT DOCUMENTS

| | | | | |
|---|---|---|---|---|
| 4,297,230 | A * | 10/1981 | Rasser | C11D 9/02 |
| | | | | 510/147 |
| 6,007,831 | A | 12/1999 | Fujiwara et al. | |
| 10,793,808 | B2 | 10/2020 | Smith | |
| 11,530,372 | B2 * | 12/2022 | Smith | C11D 3/225 |
| 2019/0284513 | A1 * | 9/2019 | Astolfi | C11D 17/006 |
| 2020/0399566 | A1 * | 12/2020 | Smith | C11D 9/442 |
| 2023/0073393 | A1 * | 3/2023 | Astolfi | C11D 9/10 |

FOREIGN PATENT DOCUMENTS

WO WO-2015189566 A1 * 12/2015 ............. A01N 25/30

OTHER PUBLICATIONS https://meliorameansbetter.com/products/foaming-hand-soap-refill-tablets Meliora.

* cited by examiner

*Primary Examiner* — Necholus Ogden, Jr.

(57) ABSTRACT

Natural green, environmentally friendly solid soap compositions and methods of manufacturing and using the same are provided with easy dispersal in water and self thickening to produce liquid soaps. The natural soap compositions contain potassium fatty acid carboxylates and preferably potassium chloride but may alternately contain potassium bromide or potassium iodide. There is a need for natural, green, environmentally friendly soaps as well as eco green packaging. Recent systems have managed eco packaging but continue to rely on synthetic non-natural fossil fuel based soaps. The inventive natural solid soaps do not require plastic or similar packaging for liquids and can be shipped as a solid bar, granules, powder, etc. and diluted very easily by the end user. Preferably the soaps are small bars that easily fit into a dispenser bottle offering versatility in concentration, lather, and thickness.

19 Claims, No Drawings

SUSTAINABLE GREEN SOLID POTASSIUM FATTY ACID SOAPS AND SELF THICKENING LIQUID SOAPS MADE THEREOF

CROSS-REFERENCE TO RELATED APPLICATIONS

Provisional application No. 63/338,606, filed on May 5, 2022.

FIELD OF THE INVENTION

The present invention relates to sustainable green potassium fatty acid solid soaps and the liquid soaps made from these solid soaps. The inventive soaps are environmentally friendly and human healthy as they do not require single use plastic or shipping of water and contain no synthetic or fossil fuel based ingredients and need no preservatives of any kind due to their short water based shelf life in use. The soaps contain additional potassium salts that may include potassium chloride (KCl), potassium bromide (KBr) or potassium iodide (KI). These additional potassium salts are very heat and shelf stable and aid in easy dispersal and self thickening when the solid soaps are dispersed in water. The solid soaps may be made in various forms such as rectangular, round or square bars, segmented bars, pellets, tablets, cubes, balls, sheets, granules, grated bars or powders. The soaps lather and clean well with good skin feel. The ease of dispersal and the thickened liquid soaps made from the solid soaps are quite unlike soaps made with either all sodium hydroxide (NaOH) lye or dual lyes containing both NaOH and potassium hydroxide (KOH) or even soaps made with all KOH. They are also very unlike soaps thickened with sodium chloride (NaCl) or even combinations of NaCl and KCl.

BACKGROUND OF THE INVENTION

Soap can be defined as a salt of one or more of the longer chain fatty acids with an alkali or metal. Most soaps are made by the action of KOH or NaOH on animal fats and vegetable oils (or free fatty acids). The preparation of soap from the oils or free fatty acids is known as saponification, which is well known in the art.

Sodium fatty acid bar soaps are well known in the art. Potassium liquid soaps are well known in the art. dual lye sodium and potassium fatty acid blend bar soaps are well known in the art. Liquid soaps thickened with NaCl are well known in the art.

Sodium fatty acid bar soaps made with NaOH cannot easily be made into liquid soap by water dilution as they form curds and gelatinous phases. Potassium fatty acid pastes made from KOH are typically further diluted slowly and with some difficulty but successfully with water to produce water thin or naturally thickened liquid soaps. The natural thickening due to the soap itself depends greatly on the type of oils or free fatty acids used in the saponification. Coconut oil and lauric acid fatty acid liquid soaps are especially hard to thicken. Exemplifying this fact Jackie Thompson in LIQUID SOAPMAKING states "But how to thicken coconut liquid soaps which are the runniest, wateriest of all natural soaps. Hydroxyethylcellulose (HEC) is the only solution I have found". This is especially problematic if you want thickened liquid soap since coconut oil or lauric acid are almost universally required if you desire bubbly lather. Olive oil or oleic fatty acid soaps thicken the most of natural oils or fatty acids but do not produce as much bubbly lather and can often produce slimy or gelatinous liquids. Combinations of the two types of oils or fatty acids also do not thicken well unless there is only a small amount of coconut oil or lauric acid. NaCl may be added to some of these soaps that are not naturally thickened after dilution with water. However, the window of effectiveness for the amount of NaCl to add is narrow and even if initially correct, on standing the soap may crystallize, separate or over thicken.

Natural fatty acid liquid soaps are growing in popularity due to sustainable, "eco" and "green" movements and concerns over climate change for synthetic soaps based on fossil fuels. However, these natural fatty acid liquid soaps suffer from having to be shipped in plastic or even single use plastic which is not sustainable, "eco" or 'green". Recently several companies have begun marketing so called sustainable "eco" soaps. SOAPBOTTLE is a liquid soap in "bottles" made of soap with wax covering. BOCKS, INC. has recently marketed fatty acid based liquid soap branded as CLEANCULT in a milk carton or gamble top type carton. Many more have recently begun to eliminate single use plastics by marketing tablets, powders or sheets of synthetic soap derived from fossil fuels which are added to refillable pump foamer bottles and shaken to dissolve to make thin liquid soap. The very dilute soaps lather by using the mechanical advantage of the foamer pumps that use air injection chambers. Foamer pumps are a type of pump that requires thin liquid soaps to function and generally require thickened liquid soaps to be diluted an additional 4-5 times to work often with reduced active soap levels which do not have a luxurious feel. Many of these new refill soaps still sell plastic bottles or plastic pumps. MELIORA recently began marketing foaming hand soap refills with six half ounce tablets in a box. Each half ounce tablet is to be added to 8 ounces of water in a foamer bottle. The tablet slowly dissolves to make thin dilute liquid soap. MELIORA is seemingly unique in offering real solid non synthetic non fossil fuel based potassium fatty acid soaps that can make thin liquid soap for foamer bottles. These tablets, however, cannot be used to make a thickened liquid soap. BLUELAND has also recently marketed refill kits using synthetic or fossil fuel based ingredient soap powders in non-plastic pouches that are dissolved in soap foamer bottles by the end user. BLUELAND sells hand and body refill pouches and starter kits including refillable glass bottles with plastic pumps. These and other recent products have done well in the market place indicating a strong desire and need for such products and systems. Of the myriad of products entering the market only BLUELAND's body soap powder appears to thicken on dilution by the end user. BLUELAND body soap lists thickening ingredients on their label that include sodium hydroxypropyl starch phosphate, acacia gum and xanthan gum. The diluted soap is an opaque thick liquid but does not have bubbly lather. The self-thickening is especially desirable for shower use or even sink use in non-foamer pumps. It is desirable to have a refillable non plastic environmentally sustainable packaging system that uses concentrated solid soaps and water used by the end user to easily make self-thickening liquid soap. Even more preferred in these systems would be real natural fatty acid soap that is not synthetic, man made or based on fossil fuels.

In addition to liquid fatty acid carboxylate soaps cream soaps and shaving soaps are well known in the art as fatty acid soaps. The cream soaps are pastes while the shaving soaps may be pastes or solid pucks. These are typically produced using dual lyes. Shaving soaps, for example are typically 60:40 KOH:NaOH. It would be desirable to have a more facile process for producing these soaps and green packaging.

SUMMARY OF THE INVENTION

In one embodiment, solid soap compositions comprise a potassium fatty acid carboxylate and a potassium salt including KCl, KBr or KI wherein the compositions have less than 2% by weight sodium.

In another embodiment the solid soap has a hardness of at least 5 kg/cm$^2$ when measured using a fruit penetrometer.

In another embodiment the solid soap composition has 12-30% by weight of potassium. In an even more preferred embodiment the solid soap composition has 15-25% by weight of potassium.

In another embodiment the solid soap composition dissolves in water to form a liquid soap having a viscosity of at least 100 cps as measured by a Zahn #5 cup viscometer at 20° C.

In another embodiment the liquid soap produced from the solid soap composition has a viscosity of at least 1000 cps as measured by a Zahn #5 cup viscometer at 20° C. In further embodiments the liquid soap produced from the solid soap composition has a viscosity of at least 2000 cps, 5000 cps, 10,000 cps, 20,000 cps, 30,000 cps, or 40,000 cps as measured by a rotary viscometer at 20° C.

In another embodiment the solid soap comprises at least 30% of the potassium fatty acid carboxylate based on the weight of the solid soap.

In another embodiment the solid soap comprises at least 10% by weight of the potassium salt.

In another embodiment the potassium fatty acid carboxylate comprises at least 40% by weight potassium oleate, at least 10% potassium laurate and at least 2% potassium stearate.

In another embodiment the potassium fatty acid carboxylate comprises greater than 20% potassium laurate, and the potassium salt is KCl.

In another embodiment the soap composition further comprises one or more of a chelator, a hardening agent, colorants, fragrances, antioxidants, hardeners, sugars, sugar alcohols, honey, pine resins, rosin, sugar alcohols, beer, and oil or water infusions of plant material.

In another embodiment the solid soap composition comprises the reaction product of:
 (a) potassium hydroxide;
 (b) a reactant selected from the group consisting of fatty triglycerides, fatty acids and combinations thereof; and
 (c) a potassium salt selected from the group consisting of potassium chloride, potassium bromide, and potassium iodide; wherein the solid soap compositions is solid at ambient conditions and has less than 2% by weight of sodium.

In another embodiment a method comprises reacting in water (i) a potassium salt selected from the group consisting of potassium chloride, potassium bromide, and potassium iodide; (ii) a reactant selected from the group consisting of fatty triglycerides, fatty acids and combinations thereof; and potassium hydroxide to form a potassium soap wherein the soap has less than 2% by weight sodium and the reaction product becomes solid at ambient conditions. Water may optionally removed before drying.

In another embodiment drying includes spray drying, drum drying, or drying in a mold.

In another embodiment the liquid soap, cream soap or shaving soap with no additional thickeners has a viscosity of at least 1000 cps as measured by a Zahn #5 viscometer at 20 degrees ° C.

In another embodiment a kit for use in making liquid soap comprises the inventive solid soap and a dispenser glass pump bottle, silicone squeeze bottle, or silicone flip top bottle or multiple such bottles.

In another embodiment the solid soap is used as a hand soap, facial soap, body soap, shampoo, shaving soap, dish soap, laundry soap, multi surface cleaner, or toilet cleaner.

In another embodiment the potassium salt is KCl.

In another embodiment the solid soap is made by hot process batch cast methods.

In another embodiment the solid soap is made by continuous process methods.

In another embodiment the solid soap is made by the process of:
 a. adding to a reactor water; a potassium salt selected from the group consisting of KCl, KBr, and KI; a reactant selected from the group consisting of fatty triglycerides, fatty acids and combinations thereof;
 b. heating the reactor to at least 200° F. (93° C.);
 c. adding to the reactor a KOH solution, the KOH solution being at a temperature of at least 200° F. (93° C.);
 d. allowing to react for at least 5 minutes; and
 e. transferring the soap into a mold or other location to harden.

In another embodiment the solid soap is a rectangular, round or square bar, segmented bar, pellet, tablet, cube, ball, sheet, granule, grated bar, or powder.

In another embodiment the potassium fatty acid carboxylate comprises more than 50%, 60%, 70%, 80%, 90% of the surfactant in the solid soap composition or is preferably essentially 100% of the surfactant in the solid soap.

In another embodiment a liquid soap, cream soap or shaving soap is made from the solid soap by water dilution.

DETAILED DESCRIPTION OF THE INVENTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are presented only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be intended to be accorded the widest possible scope consistent with the principles and features disclosed herein.

The present invention relates to solid soap compositions comprising potassium fatty acid carboxylates and a potassium salt selected from the group consisting of KCl, KBr and KI. By fatty acid soap is meant a C8 to C22 (preferably C12-C18) saturated or unsaturated, substituted or unsubstituted, branched or unbranched carboxylic acid soap. The potassium fatty acid carboxylates may be neutralized and combined with the additional potassium salt or prepared by saponification in-situ with KOH and the potassium salt.

The present invention relates to "solid" soaps. By "solid" is meant rectangular, round or square bars, segmented bars, pellets, tablets, small cubes, balls, sheets, granules, grated bars, or powders. The solid soaps in bar form have a hardness as measured by a fruit penetrometer of >1 kg/cm$^2$, preferably >5 kg/cm$^2$, most preferably >10 kg/cm$^2$ or even >20 kg/cm$^2$. The solid soaps are preferably of a size or form that allows easy addition to an opening in a dispenser such as a glass soap pump or silicone squeeze bottle or silicone flip spout bottle. If in tablet form a preferred size may be in the range of 5 grams and a half inch or so in thickness to allow this easy addition to a dispenser. This size also allows for great versatility in the number of tablets used. Water is added to the dispenser either before or after the soap addition. The water may be preheated or not. The water may be plain tap water or other natural source or may preferably be purified water such as distilled water, softened water or reverse osmosis water.

The present invention relates to "easily dispersed" bar soaps. By "easily dispersed" is meant that coarsely grated shavings from a soap bar may be easily dispersed by stirring 1.5 parts water with 1 part of the grated soap shavings at 20° C. with a fork so that it disperses well in less than 15 minutes. Of course using warm or hot water or another heat source would further speed dispersal or dissolution. The inventor has found that the inventive compositions often disperse easily in water in 10 or even 5 minutes or less using the referenced test method. The use of saponified coconut oil or lauric acid fatty acid carboxylate especially speeds dispersal. The preferred dilutions of the inventive soaps are often greater than 1.5 parts water to 1 part soap. The inventor has found that some of the inventive soaps may be diluted as much as 5 parts water to 1 part soap and still afford a high viscosity without separation or "salting out" as is common with NaCl. It has been found possible to make uniform non separated gels of many of the soaps at a 4:1 or even higher water:soap dilution.

The present invention relates to "hot process cast methods". By "hot process cast methods" is meant what is typically referred to as "HP" soap or "HTHP" soap. Oils and lye are mixed at elevated temperatures of about 200° F. (93° C.) or more for saponification to a fluid mixture that is then transferred to molds or other locations for hardening.

Although not intended to be bound by theory the inventor was extremely surprised at the easy dispersal in water but then observed later in investigations that the soap solid became cold on water dilution and surmised that maybe the easy dispersibility of the inventive soap may be at least partially due to the high enthalpy of solution of the potassium salts (such as KCl) in water. Table 1 lists the enthalpies of solution for potentially useful salts including KCl. Although there are potassium salts with higher enthalpies of dissolution than KCl (for example KBr, KI, potassium nitrate) that may work even better these are not as inexpensive or environmentally sound or safe. Non potassium salts such as sodium nitrate, ammonium nitrate, ammonium chloride, ammonium bromide, silver chloride, silver bromide, silver nitrate or silver sulfate also have high enthalpies of solution and may work but these are generally more expensive and do not contain potassium (which is deemed important in the invention for lather and viscosity and other reasons). Chloride, bromide or iodide, especially chloride, are the preferred anions as they provide the desired thickening.

TABLE 1

Enthalpies of Solution at 25° C. of Selected Anions in Water (in kJ/mol)

| CATION | ANION | | | | |
|---|---|---|---|---|---|
| | fluoride | chloride | bromide | nitrate | sulfate |
| lithium | 5 | −37 | −49 | −2 | −30 |
| sodium | 1 | 4 | −1 | 21 | 2 |
| potassium | −18 | 17 | 20 | 35 | 24 |
| ammonium | −1 | 15 | 17 | 26 | 7 |
| silver | −23 | 66 | 84 | 23 | 18 |

The invention will now be described in greater detail below.

Soap

The present invention relates to potassium fatty acid soap compositions, soap bars, soap pastes, liquids and creams.

The potassium fatty acid carboxylate soaps may be produced by neutralization of free fatty acids or saponification of animal or plant oils to produce the fatty acid salts. These fatty acids or fatty acid salts include but are not limited to saturated fatty acids such as caprylic (C8), capric (C10), lauric (C12), myristic (C14), palmitic (C16), stearic (C18), 12-hydroxy stearate (C18), unsaturated fatty acids such as ricinioleic (C18), oleic (C18), linoleic (C18), linolenic (C18), erucic (C22) as well as branched fatty acids, either saturated or unsaturated. Odd carbon fatty acids may also be used although not preferred as they are usually not natural. The oils or fats include but are not limited to almond, apricot kernel, argan, avocado, babassu, baobab, black cumin, borage, camelina, cam ilia, canola, castor, castor wax, cherry kernel oil, chicken fat, cocoa butter, coconut, coffee bean oil, cohene oil, corn oil, cottonseed, cranberry seed, crisco, cupuacu, duck fat, emu, evening primrose, flax, ghee, goose fat, grapeseed, hazelnut, hemp, horse, illipe, jatropha, jojoba, karanji, kokurn, kpangnan, kukui, lanolin, lard, laurel fruit, linseed, loofa seed, macadamia, mango seed, marula, meadowfoam, milk fat, mink oil, monoi de Tahiti, moringa, mowrah, murmura, mustard, neatsfoot, neem, oat, olive, ostrich, palm kernel, palm, papaya seed, peach, peanut, perilla, pine tar, pistachio, plum kernel, pomegranate, poppy seed, pumpkin seed, rabbit fat, rapeseed, red palm butter, rice bran oil, rosehip, sacha inchi, safflower, sal butter, saw palmetto, sea buckthorn, sesame seed, shea butter, soybean, sunflower, tallow of various animals, tamanu, tucuma, ucuuba, walnut, wheat germ, yangu and zapote seed.

The oils or fatty acids are chosen to optimize lather, skin feel, hardness of the solid soap, viscosity of the liquid soap, ease of dispersion, speed of saponification, cleaning, conditioning and shelf life. Lather and skin feel are important attributes of fatty acid soaps. NaCl is known to inhibit bubbles and it would be desirable to not inhibit bubbles as well as maintain a good skin feel. NaCl salt bars also suffer from being brittle and liable to cracking and it would be desirable to have a self-thickening bar that was not prone to cracking. The inventor has found potassium chloride bars to be surprisingly much less liable to cracking than sodium chloride bars. Coconut oil based potassium fatty acid soap is known in the art and revered as it can lather well even in seawater due to its very high water solubility. The water solubility has been reported to be 2.6 g/L for the potassium cocoate vs 0.0043 g/L for the sodium cocoate, a 600 fold difference. It is also known in the art that potassium cocoate liquid soaps cannot be thickened naturally with just the saponified oil or with NaCl salt addition as is common with other oils due to its very high soap solubility. It would be desirable to have a natural environmentally sustainable coconut oil or lauric acid fatty acid liquid soap that is thickened. Even more preferably this thickened liquid coconut oil soap would ideally be easily made from a solid soap that requires no plastic packaging or water shipment. The inventor has suprisingly found that coconut oil soaps (or high lauric fatty acid soaps) can be thickened much more readily with potassium chloride than with sodium chloride.

Sodium fatty acid soaps are produced similarly to potassium fatty acid soaps except using NaOH lye in place of KOH lye.

Blends of the lyes called "dual lyes" may also be used in some embodiments although very low sodium levels are desired.

Salt

NaCl or NaCl, plain table salt, is well known in the art in soaps for thickening, making salt bars (higher amounts of salt), brine soap (lower amounts of salt) or salting out soap. KCl or "lite" salt is less known for the use of soap. Both NaCl and KCl occur naturally as minerals in the earth. Besides the preferred KCl other potassium salts may be used including but not limited to KBr, KI, potassium citrate, potassium gluconate, potassium bitartrate, potassium nitrate, potassium acetate, potassium carbonate, potassium sulfate, and potassium salts of amino acids. KCl is preferred as it has a very high potassium content by weight and has a solubility that is not too high or too low and is very inexpensive and relatively environmentally sound. KCl is also less hygroscopic than the commonly used sodium chloride or even the very deliquescent lithium chloride (LiCl). This is extremely important in formulating a potassium bar soap to be hard under humid conditions. The lower hygroscopic behavior of KCl over NaCl and LiCl is clearly indicated by the calibration standards used for passive humidity control. Lithium chloride is used to calibrate to about 11% relative humidity (RH) over 0-60° C., sodium chloride to 75% RH over 0-35° C. and potassium chloride 80-89% RH over 0-60° C. The lower RH maintained indicates the salt prefers to hold on to water. Cesium chloride and rubidium chloride would be expected to be useful also but are prohibitively expensive.

Other Surfactants

Although the potassium fatty acid soaps are the surfactant of choice, the compositions may comprise small amounts of other surfactants selected from anionic, nonionic, zwitterionic and cationic surfactants (preferably less than 50% of the total surfactant of the composition, more preferably less than 25% by weight of the total surfactant and most preferably 0% of the total surfactant of the composition).

Other Additives

The potassium fatty acid soaps may also contain various amounts of water, other chloride salts, colorants, fragrances, essential oils, chelators, antioxidants, hardeners, sugars, sugar alcohols, honey, pine resins, rosin, sugar alcohols, beer, and oil or water infusions of plant material. Hardeners found useful include potassium lactate, potassium stearate, potassium 12-hydroxystearate and erythritol. Chelators found useful include potassium gluconate and potassium citrate.

Antimicrobial Compositions

The most effective combinations for antimicrobial effect would appear to be KCl and essentially all potassium fatty acid carboxylates (essentially no sodium fatty acid carboxylates) with greater than 50% by weight of the potassium fatty acid carboxylate being potassium laurate.

Water

The fatty acid carboxylate soaps may be made using batch "hot process" (HP) or "very high temperature hot process" (VHTHP) mold cast techniques in which water amounts are described in the art as water:oil ratio. For the purposes of this invention lower water:oil ratios are preferred as it speeds saponification although saponification may proceed slowly and completely with time at higher ratios. Higher ratios may also be desired to allow time to work with additives, prevent extreme exotherms ("volcanoes") or to create different effects. 1:1 ratios are the lowest usually used for NaOH as that is maximum solubility at room temperature. KOH is however more water soluble and a ratio as low as 0.9:1 ratio or even lower may be acceptable.

The fatty acids may be combined directly with the potassium salt and other additives and neutralized with lye or the saponification may be done by continuous processes, spray drying to powders, extruding, milling, etc. that may require different amounts of water.

TFM (Total Fatty Matter)

The TFM or total fatty matter is an industry accepted term for quality of soaps and is defined as the total amount of fatty matter, mostly fatty acids, that can be separated from a sample after splitting with mineral acid, usually hydrochloric acid. The inventive compositions typically have 30-70% TFM although it may vary depending on the oils and use desired.

Sodium, Potassium and Chloride

Sodium, potassium and chloride levels can easily be measured with test strips, portable meters or very quantitatively in a lab with ion selective electrodes or flame photometers. In a molding operation it is very important for the soap to harden quickly to enable economical, facile and timely unmolding. To that end sodium levels should be kept below 2% by weight of the soap to avoid soft bars that are formed in high K soaps. Potassium levels are preferably 12-30% by weight of the soap and most preferably 15-25%. Lower potassium levels may not afford sufficient thickening and higher levels may make unacceptably low % soap actives.

Superfat (SF)

SF is the % excess fat or oil intentionally or unintentionally remaining in the saponified soap. For situations where the bars are not intended to be diluted with further water it may be desirable to use a higher SF (as high as 20% or so) for more drying oils like coconut. For bars desired to be diluted with water it is better to keep SF to only 0-3% or so to avoid cloudiness or separation in the liquids produced.

Curing

Those skilled in the art generally "cure" soaps by allowing them to stand in well ventilated low humidity dark areas for 4-6 weeks and even up to a year for castille (olive oil) type HP cast soaps. "Curing" soap is defined as allowing it to age, mature and dry out. Curing essentially is water evaporation or possibly also some completion of saponification. After unmolding one can measure hardness and weight over time as an indication of cure.

Preservatives

Solid fatty acid bar soaps generally do not require an antimicrobial preservative due to their high pH and low water activity. Liquid fatty acid soaps or any liquid soaps will require a preservative as the shelf life of these high water activity soaps has to be long to allow commercial storage and shipment. Commercial liquid soaps use many preservatives which may have deleterious health or environmental effects. Examples of commercial preservatives used in natural fatty acid liquid soaps include "LINCOSERV HPH-2" which is globally approved for high pH, is heat stable and has mostly natural additives (benzyl alcohol and capyryl glycol) combined with a synthetic preservative (phenoxyethanol). Other less preferable preservatives used in fatty acid liquid soaps are formaldehyde releasers, "QUARTERNIUM-15" or isothiazolinone.

The inventive solid soap compositions are to be diluted by the end user to a liquid soap and thus do not require a preservative if the end user consumes the diluted soap within about 6 months. The salt of the inventive composition may also act in some capacity as a preservative. However, preservatives may be added to the inventive solid soap during final processing while still fluid.

EXAMPLES

Method of Manufacture

Two methods of manufacture were used in the examples. These are heretofore referred to as "bottle method" and "HTHP kettle method". All examples used 0% superfat.

The "bottle process" is that described by Kevin Dunn in SCIENTIFIC SOAPMAKING where screw cap heavy walled polypropylene bottles of various sizes are used to shake and swirl the oils and lye and salts for saponification before pouring into molds. Typically the salts, additives, hot oils, and hot water are added to the bottles and mixed and then hot dissolved lye is added and the bottles shaken for under a minute and swirled occasionally until a proper "trace" is reached. "Trace" refers to the degree of saponification as evidenced by the viscosity increase or the dropping of the soap "batter" onto the surface of the batter to see if it sinks or leaves a trace. "Trace" usually happens after emulsification. Heavy trace means more saponification or viscosity. The bottles may be further heated in a microwave or other means before pouring into molds. It has been found that higher temperatures are desired in the invention so that temperatures as close to 200° F. were used as possible without warping bottles. In my process I have altered Kevin Dunn's procedure of placing in a roaster oven for 4 hours at 140° F. by using a large dehydrator and placing the molds in the dehydrator to complete saponification for 4 hours at 160° F. The molds are then removed and allowed to stand or placed in a freezer if necessary before unmolding. In all the examples that used this procedure I used a water:lye ratio of 1.5:1 which required a lye master batch of 50% lye and some additional water.

The "HTHP kettle process" is done in a KITCHEN AID mixer with a digital heater bowl. The bowl and oils are preheated on the maximum digital setting of 220° F., the salt is added followed by hot (170-180° F.) 50% lye. I used a 1:1 water:lye ratio and 50% lye master batch in all the examples with this method so no additional water was required. After the hot lye was added an immersion blender was used in short bursts for 1-2 minutes until a "vaseline" stage appeared and then the batch was stirred with a spatula until temperatures reached 220-235° F. These exotherms were often rapid and accompanied by a so called "volcano" that was accommodated by doing 600 g batches in the large 4 liter mixer. After the exotherm to 220-235° F., 3% of a 60% sodium lactate solution was added to thin the batter and also allow for a harder bar. Then spatula mixing was continued along with the external heating (still kept at heater setting of 220° F.) until a "mashed potato" stage was reached but not too thick to transfer to the molds. The batter was transferred to molds and treated as in the "bottle method". In all examples "100% KOH" means no NaOH was added and all KOH lye was used for 100% saponification with 0% SF.

Hardness Testing

Bar hardness was measured by a fruit penetrometer. The specific fruit penetrometer used was a NEWTRY Model GY-3 with two spindles for low and high range hardness. It is capable of measuring hardness up to 24 kg/cm2. The spring loaded device with a dial is pressed into the soap until the penetrometer reaches a depth indicated by a line and a dial reading is taken.

Lather Testing

Lather testing was done by simple hand washing with the bars

Skin Feel

Skin feel was simple observation during and after washing hands

Dilution

The samples were tested for easy dispersibility by adding 1.5 parts water to 1 part coarse grated shavings of the soap at 20 C and stirring with a fork. Uniform dispersion in less than 15 minutes is considered "easily dispersed".

Comparative Example A

100% coconut, 100% NaOH, 50% NaCl (NaCl based on oils weight)
"Bottle Process"
Hard bright white abrasive feeling bar. Hardness after unmolding is >24 kg/cm2. 1.5:1 dilution with water results in an unacceptable thin curdy separated liquid.

Comparative Example B

100% coconut oil, 100% KOH, no salts
"HTHP Kettle Process"
Hard translucent amber colored hard bars. Hardness 4.5 kg/cm2 1 day after unmolding. 5.5 kg/cm2 after 1 week. 1.5:1 dilution was not easily dispersed and took a very long unacceptable time to disperse (several hours).

Comparative Example C

100% coconut oil, various dual lye ratios of KOH:NaOH, No salt
"Bottle Process"
Batches of 100% KOH, 95:5 KOH:NaOH, 90:10 KOH:NaOH, 80:20 KOH:NaOH, 70:30 KOH:NaOH, 60:40 KOH:NaOH were made. No salt and all coconut oil were used. All bars were hard after unmolding within a day of pouring. 4-6 kg/cm2. The 100% KOH bar did not easily disperse in water and took several hours, eventually forming a clear thin liquid soap.

Example 1

100% coconut oil, 100% KOH, 50% KCl (KCl based on oil weight)
"Bottle Process"
Hard slightly translucent bars 5 kg/cm2 a few days after unmolding. Easily dispersed in water. 1.5:1 dilution resulted in a nicely thickened translucent liquid soap. Good lather and skin feel.

Example 2

65% coconut oil, 20% rice bran oil, 10% palm oil, 5% castor oil.
100% KOH, 150% KCl (KCl based on oils weight)
"HTHP Kettle Process".
Hard slightly translucent bars 5 kg/cm2 a few days after unmolding. Easily dispersed in water. Extremely thick liquid soap after 1.5:1 dilution. Good lather and skin feel.

Example 3

65% coconut oil, 20% rice bran oil, 10% palm oil, 5% castor oil.
100% KOH, 100% KCl (KCl based on oils weight)
"HTHP Kettle Process".
Hard slightly translucent bars 4 kg/cm2 a few days after unmolding. Easily dispersed in water. Very thick liquid soap after 1.5:1 dilution. Good lather and skin feel.

Example 4

65% coconut oil, 20% rice bran oil, 10% palm oil, 5% castor oil.
100% KOH, 50% KCl (KCl based on oils weight)
"HTHP Kettle Process"
Hard slightly translucent bars 7 kg/cm2 a few days after unmolding. 1.5:1 dilution easily dispersed and nicely thickened to a translucent liquid soap.
Good lather and skin feel.

Example 5

65% coconut oil, 20% rice bran oil, 10% palm oil, 5% castor oil.
100% KOH, 25% KCl (KCl based on oils weight)
Hard semi translucent light amber colored bars 4.5 kg/cm2 a few days after unmolding. Good lather and skin feel. 1.5:1 dilution easily dispersed and slightly thickened translucent to clear liquid soap.

Example 6

65% coconut oil, 20% rice bran oil, 10% palm oil, 5% castor oil.
100% KOH, 10% KCl (KCl based on oils weight)
Nice looking semi hard translucent dark amber colored bars. 3.5 kg/cm2 a few days after unmolding. 1.5:1 dilution easily dispersed with water to form only a very slightly thickened watery clear translucent liquid soap. Good lather and skin feel.

Example 7

65% coconut oil, 20% rice bran oil, 10% palm oil, 5% castor oil.
100% KOH, 5% KCl (KCl based on oils weight)
Semi hard translucent amber colored bars. 2.5 kg/cm2 a few days after unmolding. 1.5:1 dilution easily dispersed with water to form watery clear thin translucent liquid soap. Good lather and skin feel.

Example 8

65% coconut oil, 20% rice bran oil, 10% palm oil, 5% castor oil.
100% KOH, 25% KCl, 25% NaCl (salts based on oils weight)
A hard bar 3.5 kg/cm2 a week after unmolding. 1.5:1 water to soap dilution easily dispersed to a very thick pearlescent liquid soap. Good lather and skin feel.

Example 9

65% coconut oil, 20% rice bran oil, 10% palm oil, 5% castor oil
100% KOH, 40% KCl, 10% NaCl (salts based on oils weight)
"HTHP Kettle Process"
Soft off white bars. 0.5 kg/cm2 a few days after unmolding. However, after a week after unmolding the bars were harder than 1 kg/cm2. 1.5:1 dilution easily dispersed to form a very thick, translucent, pearlescent liquid soap. Good lather and skin feel.

Example 10

Coconut:castor ratio blends with 100% KOH and 50% KCl (KCl based on oils weight)
"Bottle Process"
100% coconut, 95:5 coconut:castor, 90:10 coconut:castor, 85:15 coconut:castor, 80:20 coconut:castor, 75:25 coconut:castor bars were made.
The bars had good lather and the lather increased with increasing castor oil amounts. There was no sticky feeling after washing even with 25% castor. The hardness measurements 24 hours after unmolding were all 4-5 kg/cm2. The 1.5:1 dilutions easily dispersed but the higher castor bars dispersed slightly slower than the lower castor bars. Increasing castor levels had increased translucency and lower viscosity on 1.5:1 dilution. Overall the dilutions went from fairly low viscosity with the 75:25 to higher viscosity but still not very thick for the 95:5. Good lather and skin feel.

Example 11

75% deer tallow, 25% coconut, 100% KOH, 50% KCl (KCl based on oils weight)
"HTHP Kettle Process"
Hard opaque white bars. 6 kg/cm2 a few days after unmolding. Dispersed easily in water. 1.5:1 water dilution resulted in a very thick uniform cream soap. Good lather and skin feel.

Example 12

85% olive oil, 15% castor oil, 100% KOH, 50% KCl (KCl based on oils weight)
"HTHP Kettle Process"
Bars hard but softer than 100% coconut or 65:20:10:5 or coconut castor blends. 4 kg/cm2 at 5 days after unmolding. 1.5:1 dilution with water easily dispersed to a medium viscosity uniform light cream soap. Good lather and skin feel.

Example 13

100% coconut, 100% KOH, 50% KBr (salt based on total batch weight)
"Bottle Process"
Hard opaque partially translucent bars 5.5 kg/cm2 several days after unmolding. Trace faster than Kbitartrate but slower than KCl or Kcitrate.
1.5:1 dilution thickened and easily dispersed. Lathers well. Good skin feel.

Example 14

100% coconut, 100% KOH, 50% Kbitartrate in-situ converted to dipotassium salt (salt based on total batch weight)

"Bottle Process"
Slowest trace of all the potassium salts tested.
Hard bars 6.5 kg/cm2 a week after unmolding.
1.5:1 dilution slightly thickened and easily dispersed. Good lather and skin feel.

Example 15

100% coconut, 100% KOH, 50% Kgluconate (salt based on oil wt)
"Bottle Process"
Hard opaque white bars >24 kg/cm2 several days after unmolding.
Trace faster than Kbitartrate but slower than KCl or Kcitrate or KBr.
1.5:1 dilution thickened slightly and easily dispersed. Good lather and skin feel.

Example 16

100% coconut, 100% KOH, 50% Kcitrate salt based on oil weight)
"Bottle Process"
Hard opaque white bars >24 kg/cm2 several days after unmolding.
Trace faster than all K salts tested except KCl. 1.5:1 dilution thickened slightly and easily dispersed. Good lather and skin feel.

Example 17

100% coconut oil, 100% NaOH, 50% KCl (KCl based on oil weight)
"Bottle Process"
Hard opaque partially translucent bars 5.5 kg/cm2 several days after unmolding.
Trace fastest of all K salts tested. 1.5:1 dilution easily dispersed and thickened to a translucent to clear very thick liquid creamy soap. Good lather and skin feel.

Additional testing was done to exemplify the distinct and unique advantages of KOH and KCl over NaOH or NaCl or any sodium salts in the inventive soaps and the disadvantage of using even small amounts of sodium. In other experiments it was found that even using 3-5% sodium lactate or sodium gluconate with no other sodium sources made for a softer bar that was hard to unmold.

Round bars measuring 2"×2"×1" were produced by pouring soap batter into silicone molds. All bars were made using an oil blend of 50% by weight olive oil, 35% by weight coconut oil and 15% by weight cocoa butter. The batches were produced using the "HTHP kettle process" except that the water: KOH ratio was 1.3 with 0% superfat and the lye was added at 200-220° F. Amounts of sodium or KCl were added into the oils before the addition of KOH as weight % of total batch as shown in Table 2. The entry labeled "60:40 dual lye" replaced the single KOH lye with a 60% KOH: 40% NaOH dual lye with the same 0% superfat. Hardness testing was done with a NEWTRY Fruit Hardness Tester Model GY-3 and the 8 mm diameter spindle which reads from 1-24 kg/cm$^2$. These soaps were used for hardness testing over time.

TABLE 2

Hardness: Sodium vs. Potassium

| | DAY 1 HARDNESS kg/cm$^2$ | DAY 3 HARDNESS kg/cm$^2$ | DAY 8 HARDNESS kg/cm$^2$ | DAY 30 HARDNESS kg/cm$^2$ |
|---|---|---|---|---|
| 0% Salt | 2.4 | 5.0 | 6.0 | 8.0 |
| 0% Salt 60:40 dual lye | ND | ND | 2.0 | 3.8 |
| 2% NaCl | 2.0 | 2.0 | 2.0 | 4.8 |
| 5% NaCl | ND | ND | ND | 3.4 |
| 5% KCl | 5.6 | 6.2 | 8.0 | 12.4 |
| 10% NaCl | 1.0 | 4.0 | 6.0 | 8.6 |
| 10% KCl | 5.8 | 6.0 | 8.0 | 12.8 |
| 15% NaCl | NM | 6.0 | 9.0 | 13.0 |
| 15% KCl | NM | 7.0 | 8.0 | 13.0 |
| 25% NaCl | 2.4 | Cracked at 1.0 | Cracked at 6.0 | Cracked at 10.2 |
| 25% KCl | 6.6 | 7.0 | 8.0 | 14.6 |
| 50% NaCl | ND | ND | Cracked at 5.4 | Cracked at 10.2 |
| 50% KCl | 9.0 | 9.0 | 12.0 | 20.2 |

ND = not detectable. Less than 0.1.
NM = not measured.

Another set of soaps and experiments was done to show the viscosity effects of sodium vs potassium. Small amounts of sodium in the high potassium soaps resulted in very soft bars that took a long time to harden. The soap was made using the "HTHP kettle process" except that no salt was used (it was pre-dissolved in the dilution water), the bars were made using an oil blend of 50% by weight olive oil, 35% by weight coconut oil and 15% by weight cocoa butter and the water: KOH ratio was 1.3 with 0% superfat. Viscosity measurements were done in triplicate using a Zahn Cup #5 at 20° C. with 200 gram samples of diluted soap (3.8:1 water:grated solid soap). The viscosity equation used was 23(t) where t is the time of elution from the cup. Measurements were made after the dilutions were left covered and standing for 24 hours. The % salt in Table 3 refers to total % salt in the diluted 200 gram test samples. Unexpectedly It was found that using even higher KCl levels than shown in the table did not cause separation or curding as in the case of NaCl and produced a uniform stable thick soap far exceeding the accuracy range of the Zahn Cup #5 (accuracy range 460-1840 cps or 20-80 seconds).

TABLE 1

Viscosity vs. % Salt

| | NaCl | KCl |
|---|---|---|
| 1.4% salt by weight | NM clear | NM. Clear. Homogenous. |
| 1.8% salt by weight | 130. Mass of salt crystals grow with time. | NM. Clear. Homogenous. |
| 2.2% salt by weight | 300. Mass of salt crystals grow with time and then gels. | NM. Clear. Homogenous. |
| 2.6% salt by weight | Thick opaque paste gels with time | NM. Clear. Homogenous. |
| 3.0% salt by weight | Very thick opaque paste gels with time | NM. Clear. Homogenous. |
| 3.4% salt by weight | Separates clear liquid on bottom and paste on top | 120. Clear. Homogenous. |
| 3.8% salt by weight | Separates clear liquid on bottom and paste on top | 250. Slightly translucent. Homogenous. |
| 4.2% salt by weight | Separates clear liquid on bottom and paste on top | 800. Translucent. Homogenous. |
| 4.6% salt by weight | Separates clear liquid on bottom and paste on top | 1500. Translucent. Homogenous. |

TABLE 1-continued

Viscosity vs. % Salt

| | NaCl | KCl |
|---|---|---|
| 5.0% salt by weight | Separates clear liquid on bottom and paste on top | 2500. Translucent. Homogenous. |

NM = not measurable (under 100 cps)

Additional testing was done to compare the 2:1 water:soap viscosities and the dispersability of the inventive soaps to competitive product MELIORA and HELLO PRODUCTS LLC. The former is potassium fatty acid soap in half ounce tablets meant to make 9 oz of foamer soap while the latter is synthetic soap powder (taurate) in 0.31 oz tablets meant to make 8 oz of foamer soap. The MELIORA and HELLO 2:1 dilutions were found to have viscosities less than 100 cps (below detectable accuracy of the Zahn Cup #5) when using the Zahn Cup #5 at Zahn Cup #5 at 20° C. while a soap of the invention was unmeasurably high with the Zahn Cup #5 as it was a homogeneous stable gel. The inventive soap tested was made from an oil blend of 50% by weight olive oil, 35% by weight coconut oil and 15% by weight cocoa butter as per the procedure for the 2"×2"×1" bars. Dispersability tests were performed on these same three products as per the previously mentioned dispersability test using grated soap. The inventive soap dispersed in 10 minutes while MELIORA took 15 minutes and HELLO took over 15 minutes, indicating the dispersing benefit of potassium chloride.

What is claimed is:

1. Solid soap compositions comprising: (a) a potassium fatty acid carboxylate; and
   (b) a potassium salt selected from the group consisting of potassium chloride, potassium bromide, potassium iodide, and combinations thereof; wherein the soap composition is solid at ambient conditions and has less than 2% by weight sodium.

2. A solid soap composition according to claim 1, wherein the solid soap composition has a hardness of at least 5 kg/cm2 when measured using a fruit penetrometer.

3. A solid soap composition according to claim 1, wherein the solid soap composition has 12-30% by weight of potassium.

4. A soap composition according to claim 1, wherein the solid soap composition dissolves in water to form a liquid soap having a viscosity of at least 100 cps as measured by a Zahn #5 viscometer at 20° C.

5. A soap composition according to claim 4, wherein the liquid soap has a viscosity of at least 1000 cps as measured by a Zahn #5 viscometer at 20° C.

6. A soap composition according to claim 5, wherein the potassium fatty acid carboxylate is greater than 20% potassium laurate, and the potassium salt is potassium chloride.

7. A soap composition according to claim 1, wherein the solid soap composition has at least 10% by weight of the potassium salt.

8. A soap composition according to claim 7, wherein potassium fatty acid carboxylate is at least 40% by weight potassium oleate, at least 10% potassium laurate, and at least 2% potassium stearate.

9. A soap composition according to claim 1, wherein the solid soap composition has at least 30% by weight of the potassium fatty acid carboxylate.

10. A soap composition according to claim 1, further comprising one or more of a chelator, a hardening agent, colorants, fragrances, antioxidants, hardeners, sugars, sugar alcohols, honey, pine resins, rosin, sugar alcohols, beer, and oil or water infusions of plant material.

11. A solid soap composition comprising the reaction product of: (a) potassium hydroxide;
   (b) a reactant selected from the group consisting of fatty triglycerides, fatty acids and combinations thereof; and
   (c) a potassium salt selected from the group consisting of potassium chloride, potassium bromide, and potassium iodide; wherein the solid soap composition is solid at ambient conditions and has less than 2% by weight of sodium.

12. A solid soap composition of claim 11, further comprising one or more of a chelator, a hardening agent, colorants, fragrances, antioxidants, hardeners, sugars, sugar alcohols, honey, pine resins, rosin, sugar alcohols, beer, and oil or water infusions of plant material.

13. A solid soap composition of claim 11, wherein the solid soap composition has 12-30% by weight of potassium.

14. A method comprising reacting in water (i) a potassium salt selected from the group consisting of potassium chloride, potassium bromide, and potassium iodide; (ii) a reactant selected from the group consisting of fatty triglycerides, fatty acids and combinations thereof; and potassium hydroxide to form a potassium soap wherein the soap has less than 2% by weight sodium and the reaction product becomes solid at ambient conditions.

15. A method according to claim 14, further comprising removing water from the potassium soap before drying.

16. A method according to claim 15, wherein drying includes spray drying, drum drying, or drying in a mold.

17. A method according to claim 14, wherein the solid soap composition has 12-30% by weight of potassium.

18. A method according to claim 14, wherein the potassium fatty acid carboxylate is at least 40% by weight potassium oleate, at least 10% potassium laurate, and at least 2% potassium stearate.

19. A method according to claim 14, further comprising one or more of a chelator, a hardening agent, colorants, fragrances, antioxidants, hardeners, sugars, sugar alcohols, honey, pine resins, rosin, sugar alcohols, beer, and oil or water infusions of plant material.

* * * * *